(12) United States Patent
Kunath et al.

(10) Patent No.: US 8,093,270 B2
(45) Date of Patent: Jan. 10, 2012

(54) SOLID PHARMACEUTICAL COMPOSITION COMPRISING (R)-(−)-2-[5-(4-FLUOROPHENYL)-3-PYRIDYLMETHYLAMINOMETHYL] CHROMAN

(75) Inventors: Klaus Kunath, Muehlheim (DE); Kirstin Heil, Darmstadt (DE); Roland Rupp, Bergisch-Gladbach (DE)

(73) Assignee: Merck Patent GmbH, Darmstadt (DE)

( * ) Notice: Subject to any disclaimer, the term of this patent is extended or adjusted under 35 U.S.C. 154(b) by 807 days.

(21) Appl. No.: 11/993,324

(22) PCT Filed: Jun. 9, 2006

(86) PCT No.: PCT/EP2006/005563
§ 371 (c)(1),
(2), (4) Date: Dec. 20, 2007

(87) PCT Pub. No.: WO2006/136302
PCT Pub. Date: Dec. 28, 2006

(65) Prior Publication Data
US 2010/0105648 A1    Apr. 29, 2010

(30) Foreign Application Priority Data
Jun. 21, 2005   (EP) ................................ 05013293

(51) Int. Cl.
*A01N 43/40* (2006.01)
*A01N 43/16* (2006.01)
*A01N 43/06* (2006.01)
*A61K 31/44* (2006.01)
*A61K 31/35* (2006.01)
*A61K 31/38* (2006.01)

(52) U.S. Cl. .......................... 514/337; 514/456; 514/444

(58) Field of Classification Search .................... 514/337
See application file for complete search history.

(56) References Cited

U.S. PATENT DOCUMENTS

| 4,327,077 A | * | 4/1982 | Puglia et al. .................. 424/441 |
| 6,136,347 A | * | 10/2000 | Pollinger et al. .............. 424/495 |
| 6,204,036 B1 | * | 3/2001 | Metzner et al. ................ 435/188 |
| 2002/0058714 A1 | | 5/2002 | Maruyama |
| 2003/0181486 A1 | | 9/2003 | Bartoszyk et al. |

FOREIGN PATENT DOCUMENTS

| EP | 1 192 942 A | 4/2002 |
| WO | WO 01/68063 A | 9/2001 |

* cited by examiner

*Primary Examiner* — Sreeni Padmanabhan
*Assistant Examiner* — Layla Soroush
(74) *Attorney, Agent, or Firm* — Millen, White, Zelano & Branigan, P.C.

(57) ABSTRACT

The invention relates to a solid pharmaceutical preparation containing (R)-(−)-2-[5-(4-fluorophenyl-3-pyridylmethy-laminomethyl]chroman as an active substance and at least one sugar alcohol (e.g. mannitol, sorbitol) as a filler. Also disclosed is the production of said solid pharmaceutical preparation, which is provided with an increased shelf life also at elevated temperatures and can be used for the treatment of dyskinesia associated with Parkinson's disease.

20 Claims, No Drawings

SOLID PHARMACEUTICAL COMPOSITION COMPRISING (R)-(−)-2-[5-(4-FLUOROPHENYL)-3-PYRIDYLMETHYLAMINOMETHYL] CHROMAN

The present invention relates to a solid pharmaceutical composition comprising (R)-(−)-2-[5-(4-fluorophenyl)-3-pyridylmethylaminomethyl]chroman as active compound and to the preparation of the solid pharmaceutical composition.

(R)-(−)-2-[5-(4-fluorophenyl)-3-pyridylmethylaminomethyl]chroman is the first representative of a new class of atypical neuroleptics which, in combination, result both in selective blockage of dopamine $D_2$ receptors ($D_2$ antagonist) and also selective stimulation of serotonin 5-$HT_{1A}$ receptors (5-$HT_{1A}$ agonist). Owing to the novel principle of action, (R)-(−)-2-[5-(4-fluorophenyl)-3-pyridylmethylaminomethyl]chroman can be employed for the treatment of schizophrenia and for the treatment of dyskinesia/psychosis in Parkinson's disease. The aim is for (R)-(−)-2-[5-(4-fluorophenyl)-3-pyridylmethylaminomethyl]chroman to be developed clinically for the treatment of dyskinesia in Parkinson's disease.

The clinical development and subsequent marketing of this active compound requires a pharmaceutical composition which is easy to administer, preferably a solid pharmaceutical composition which can be administered orally. The pharmaceutical composition should not comprise any toxicologically unacceptable adjuvants, should ensure good release of active compound and should be capable of storage in a stable manner for an extended time, even at elevated temperature and atmospheric humidity levels.

Extensive experiments have been carried out to provide a solid pharmaceutical composition which meets these requirements. However, the experiments did not give a solid pharmaceutical composition which meets these requirements, in particular repeatedly gave poor stability of the active compound (R)-(−)-2-[5-(4-fluorophenyl)-3-pyridylmethylaminomethyl]chroman.

The object of the present invention was to provide a solid formulation of (R)-(−)-2-[5-(4-fluorophenyl)-3-pyridylmethylaminomethyl]chroman suitable for oral administration which meets the above-mentioned requirements. In particular, the composition should ensure release of active compound in accordance with the requirements, should not comprise any toxicologically unacceptable adjuvants and should be capable of storage in a stable manner over an extended time in climatic zone I-IV, i.e. even at elevated temperature and atmospheric humidity levels.

Surprisingly, it was possible to provide a composition which meets these requirements if it comprises one or more sugar alcohol(s) as filler(s) in addition to the active compound. The present invention therefore relates to a solid pharmaceutical composition comprising (R)-(−)-2-[5-(4-fluorophenyl)-3-pyridylmethylaminomethyl]chroman as active compound and at least one sugar alcohol as filler.

(R)-(−)-2-[5-(4-fluorophenyl)-3-pyridylmethylaminomethyl]chroman may be present in the pharmaceutical composition as the free base or in the form of one of its acid-addition salts, such as, for example, as the hydrobromide, hydrochloride, dihydrochloride, acetate, aspartate, benzoate, citrate, fumarate, glutamate, maleate, methanesulfonate or tartrate. (R)-(−)-2-[5-(4-fluorophenyl)-3-pyridylmethylaminomethyl]chroman is preferably present as an acid-addition salt, particularly preferably as the hydrochloride salt.

The solid pharmaceutical composition according to the invention comprises one or more sugar alcohol(s). Sugar alcohols are taken to mean monosaccharides whose reactive carbonyl group has been reduced to the alcohol group, such as, for example, hexitols or pentitols. The solid composition according to the invention preferably comprises hexitols, such as, for example, mannitol, sorbitol, dulcitol, xylitol or ribitol, as sugar alcohol(s). Particular preference is given to the presence of mannitol and/or sorbitol, very particularly preferably mannitol.

The sugar alcohol(s) can be employed in all their modifications in which they occurs. For example, if the sugar alcohol employed is mannitol, this can be in the form of one or more of its polymorphic forms, for example the α-, β-, γ- or δ-modification. Mannitol is preferably employed in the form of its β- and/or δ-modification, particularly preferably in the form of its δ-modification, i.e. as δ-mannitol. The use of δ-mannitol is particularly preferred if water is added to the composition during its preparation, as takes place, for example, during moist granulation. In this case, some of the δ-mannitol is converted into β-mannitol, and the tabletting properties are improved by this conversion.

Owing to their preparation by reduction of monosaccharides, sugar alcohols may still comprise small proportions of sugars, which can have a reducing action, as a consequence of incomplete reaction of the carbonyl groups. The composition according to the invention therefore preferably comprises sugar alcohols in a quality which comprises the lowest possible content of such unreacted or incompletely reacted sugars. It is therefore preferred for the composition according to the invention to comprise sugar alcohol(s) which comprise(s) less than 0.2% by weight, particularly preferably less than 0.05% by weight, of reducing sugars.

The solid pharmaceutical composition can be in powder, granule, pellet, capsule or tablet form. While capsules and tablets provide the amount of active compound intended to be taken in each case as a clearly defined individual dose, the amount of active compound required in each case can be adapted in a simple manner by means of powders, pellets and granules. Granules are flowable granular aggregates of powders which can be prepared by granulation. Pellets are solid, small, spherical medicament forms, such as, for example, granule grains or microtablets, having a very narrow particle-size range. Granules and pellets represent an independent medicament form, but can also serve as intermediate product for the production of tablets. If it is intended that predetermined amounts of active compound can be administered by means of powders, granules or pellets, these are, in order to ensure adequate dosage accuracy, also provided as portioned powders/granules or introduced into capsules. The pharmaceutical composition according to the invention is preferably in granule, capsule or tablet form, particularly preferably in capsule or tablet form, very particularly preferably in tablet form.

Depending on the medicament form, the solid composition according to the invention may comprise various adjuvants, such as, for example, binders, additional fillers, disintegrants, flow regulators or lubricants.

Binders are employed, in particular, as adjuvants for the production of granules and capsules and tablets produced from granules and are responsible, inter alia, for the cohesion of the powder particles in the granule grain. Binders which can be employed are, for example, polymers, such as, for example, polyvinylpyrrolidone or polyvinyl acetate, starch pastes, such as, for example, maize starch paste, cellulose derivatives, such as, for example, hydroxypropylmethylcellulose or hydroxypropylcellulose. The solid composition according to the invention preferably comprises cellulose derivatives as binder, where hydroxypropylmethylcellulose is particularly preferred. Depending on the nature of the binder, this may be present in the solid composition according to the invention in a proportion of 0.1 to 80% by weight. The solid composition according to the invention preferably comprises 1 to 5% by weight, particularly preferably 1.5 to 3% by weight, of binder.

Disintegrants may be present in order to shorten the disintegration time of tablets, enabling the active compound to be released rapidly from the tablets. Examples of disintegrants which can be employed in accordance with the invention are microcrystalline cellulose, crosslinked polyvinylpyrrolidone, such as, for example, crospovidones or crosslinked carboxymethylcellulose. The solid composition according to the invention particularly preferably comprises carboxymethylcellulose, very particularly preferably crosslinked carboxymethylcellulose, as disintegrant. Depending on the nature of the disintegrant, this may be present in the solid composition according to the invention in a proportion by weight of 0.01 to 20% by weight. The solid composition according to the invention preferably comprises 0.1 to 5% by weight, particularly preferably 0.2 to 2% by weight, of disintegrant.

Flow regulators may be present in powders or granules and are admixed therewith in order to increase their flowability. Likewise, flow regulators may be present in tablets if the latter are produced by pressing powders or granules. In this case too, they are admixed with the powders/granules in order to increase their flowability, in particular in order to ensure uniform filling of the moulds before the tablet pressing and thus to ensure high dosage accuracy. Flow regulators which can be employed are, for example, highly disperse silicon dioxide (Aerosil) or dried starch. The solid composition according to the invention preferably comprises highly disperse silicon dioxide as flow regulator. Flow regulators are preferably present in the solid composition according to the invention in a proportion of 0.1 to 3% by weight, preferably 0.2 to 2% by weight, particularly preferably 0.3 to 1% by weight.

If the solid composition according to the invention is a tablet, this may also comprise lubricants in order to reduce the sliding friction of the tableting material and ram in the mould during the tableting operation and to prevent sticking to the rams. Suitable lubricants are alkaline-earth metal salts of fatty acids, such as, for example, magnesium stearate, higher fatty alcohols or talc. The solid composition according to the invention preferably comprises magnesium stearate as lubricant. Lubricants are preferably present in the solid composition according to the invention in a proportion of 0.1 to 5% by weight, preferably 0.5 to 5% by weight, particularly preferably 1 to 3% by weight.

If the solid composition according to the invention is a tablet, this may be provided with a coating. Suitable coatings are film-forming polymers, such as, for example, those from the group of the cellulose derivatives, dextrins, starches, natural gums, such as, for example, gum arabic, xanthans, alginates, polyvinyl alcohol, polymethacrylates and derivatives thereof, such as, for example, eudragites, which may be applied to the tablet as solutions or suspensions by means of the various pharmaceutical conventional methods, such as, for example, film coating. Use is usually made here of solutions/suspensions which, besides the film-forming polymer, also comprise further adjuvants, such as hydrophilisers, plasticisers, surfactants, dyes and white pigments, such as, for example, titanium dioxide.

The solid composition according to the invention can be prepared by methods known to the person skilled in the art.

Powders can be prepared, for example, by adding the sugar alcohol and optionally further adjuvants, such as flow regulators, to the active compound and subsequently mixing the components.

Granules are produced by granulation, which can basically be carried out by the moist or dry route. In the case of moist granulation, for example, a granulation liquid, which preferably comprises a binder, is added to a powder mixture comprising the active compound together with the sugar alcohol and any further suitable adjuvants, the mixture is converted into aggregates of suitable size (granules) and subsequently dried. The active compound can also be introduced into the granules by suspension in the granulation liquid. The conversion of the powder mixture into aggregates of suitable size can be carried out, for example, by so-called build-up granulation, for example in coating pans, by means of plate granulation or in fluidised-bed methods, for example by the Glatt or Wurster method, or by so-called reduction granulation, in which the powder mixture is firstly moistened and converted into a plastically mouldable mass and subsequently converted into aggregates of the desired size, for example by extrusion through a screen having meshes of suitable size. In the case of dry granulation, the powder mixture is pressed, for example, by means of compaction between two counter-rotating compaction rolls to give flakes, which are subsequently comminuted to give granules.

Pellets can be produced by granulation and subsequent rounding-off (spheronisation), for example by means of plate granulation, or alternatively by pressing powders or granules to give microtablets.

The composition according to the invention in the form of tablets can be produced by pressing powder mixtures (direct compression) or by pressing granules. In the simplest case of direct compression, the active compound is firstly mixed with the sugar alcohol (in directly compressible quality) and optionally further adjuvants, and the resultant powder mixture is pressed directly to give the solid composition according to the invention.

If the composition according to the invention is prepared in the form of a tablet by pressing granules, use can be made for this purpose of granules which have been produced by moist or dry granulation. The granules are advantageously mixed, before pressing, with a so-called outer phase comprising an adjuvant or a mixture of a plurality of adjuvants, in particular lubricants, flow regulators and/or disintegrants.

If the composition according to the invention is prepared in the form of a tablet by pressing granules produced by means of moist granulation and the granules comprise mannitol as sugar alcohol, the latter is preferably employed in the form of its δ-modification, i.e. as δ-mannitol, since δ-mannitol is at least partially converted into β-mannitol during moist granulation. This causes an increase in the surface area, which advantageously results in significantly harder tablets than if β-mannitol is employed directly.

According to a preferred embodiment of the invention, the solid composition is a tablet and comprises 0.1 to 10% by weight of (R)-(+2-[5-(4-fluorophenyl)-3-pyridylmethylaminomethyl]chroman, 50 to 99.9% by weight of mannitol and 1 to 5% by weight of hydroxypropylmethylcellulose.

According to a particularly advantageous embodiment, the solid composition is a tablet and comprises 0.2 to 2% by weight of (R)-(+2-[5-(4-fluorophenyl)-3-pyridylmethylaminomethyl]chroman, 90 to 98% by weight of mannitol and 1.5 to 3% by weight of hydroxypropylmethylcellulose.

The present patent application furthermore relates to a process for the preparation of a solid pharmaceutical composition in the form of a tablet, which is characterised in that the latter is produced by direct compression or by pressing granules produced by means of moist or dry granulation, and is subsequently optionally provided with a coating.

The working examples explain the invention without being restricted thereto.

EXAMPLE 1

Powder mixture comprising 1.0 mg of (R)-(−)-2-[5-(4-fluorophenyl)-3-pyridylmethylaminomethyl]chroman 199 mg of D-mannitol The powder mixture is prepared by mixing the active compound with mannitol.

EXAMPLE 2

Granules comprising 1.0 mg of (R)-(−)-2-[5-(4-fluorophenyl)-3-pyridylmethylaminomethyl]chroman 214.74 mg of D-mannitol 5.06 mg of hydroxypropylmethylcellulose The granules are produced by granulation of the active compound with mannitol and HPMC solution in the fluidised bed. To this end, the active compound is suspended in the HPMC solution and sprayed onto the mannitol.

EXAMPLE 3

Tablet (batch 010708) comprising 1.0 mg of (R)-(−)-2-[5-(4-fluorophenyl)-3-pyridylmethylaminomethyl]chroman 214.74 mg of D-mannitol 5.06 mg of hydroxypropylmethylcellulose 2.30 mg of croscarmellose-Na 1.15 mg of highly disperse silicon dioxide 5.75 mg of magnesium stearate The tablets are produced by granulation of the active compound with mannitol and HPMC solution in the fluidised bed. To this end, the active compound is suspended in the HPMC solution and sprayed onto the mannitol. Croscarmellose, silicon dioxide and magnesium stearate are admixed with the granules, the resultant mixture is pressed to give tablets. The tablets are transferred into HDPE bottles, stored under defined climatic conditions for predetermined times and subsequently investigated with respect to active-compound content and degradation products. Storage times, climatic conditions and the amounts of active compound and degradation products measured in each case are shown in Table 1.

TABLE 1

| Weeks | Climate (° C./% R.H.) | Packaging | Content (%) | Sum of all degradation products (%) |
| --- | --- | --- | --- | --- |
| 13 | 25/60 | HDPE | 99.19 | 0.10 |
| 26 | 25/60 | HDPE | 100.17 | 0.14 |
| 13 | 30/65 | HDPE | 98.71 | 0.14 |
| 26 | 30/65 | HDPE | 98.44 | 0.22 |
| 13 | 40/75 | HDPE | 97.88 | 0.32 |
| 26 | 40/75 | HDPE | 98.36 | 0.54 |

EXAMPLE 4

Tablet (batch 9344, directly compressible) comprising 1.0 mg of (R)-(−)-2-[5-(4-fluorophenyl)-3-pyridylmethylaminomethyl]chroman 116.2 mg of mannitol 1 mg of croscarmellose 1.8 mg of magnesium stearate The tablet constituents are mixed with one another, pressed to give tablets and transferred into glass bottles. The sealed bottles are stored under defined climatic conditions for predetermined times and subsequently investigated with respect to active-compound content and degradation products. Storage times, climatic conditions and the amounts of active compound and degradation products measured in each case are shown in Table 2.

TABLE 2

| Weeks | Climate (° C./% R.H.) | Packaging | Content (%) | Sum of all degradation products (%) |
| --- | --- | --- | --- | --- |
| 22 | 25/60 | Glass | 94.3 | 0.14 |
| 22 | 30/60 | Glass | 93.8 | 0.17 |
| 22 | 40/75 | Glass | 95.3 | 0.22 |

EXAMPLE 5

Capsule (batch 9047) containing 0.5 mg of (R)-(−)-2-[5-(4-fluorophenyl)-3-pyridylmethylaminomethyl]chroman 126.5 mg of mannitol 2.0 mg of hydroxypropylmethylcellulose 2.0 mg of magnesium stearate Hard gelatine capsule size 4

The active compound is granulated together with mannitol with an HPMC solution. The granules obtained are mixed with magnesium stearate, transferred into hard gelatine capsules and transferred into glass bottles. The sealed bottles are stored under defined climatic conditions for predetermined times and subsequently investigated with respect to active-compound content and degradation products. Storage times, climatic conditions and the amounts of active compound and degradation products measured in each case are shown in Table 3.

TABLE 3

| Weeks | Climate (° C./% R.H.) | Packaging | Content (%) | Sum of all degradation products (%) |
| --- | --- | --- | --- | --- |
| 13 | 25/60 | Glass | 97.3 | 0.08 |
| 26 | 25/60 | Glass | 95.6 | 0.34 |
| 13 | 40/75 | Glass | 96.7 | 0.20 |
| 26 | 40/75 | Glass | 95.9 | 0.95 |

COMPARATIVE EXAMPLE 1

Lactose Capsule, Batch 9314

Capsule containing 0.500 mg of (R)-(−)-2-[5-(4-fluorophenyl)-3-pyridylmethylaminomethyl]chroman 126.5 mg of finely powdered lactose 2.0 mg of hydroxypropylmethylcellulose 1.0 mg of magnesium stearate Hard gelatine capsule size 4

The active compound is granulated analogously to the method described in Example 2 with lactose with HPMC solution. The granules are mixed with magnesium stearate as lubricant and transferred into empty hard gelatine capsules, stored under defined climatic conditions and subsequently investigated with respect to active-compound content and degradation products. The results are shown in Table 4.

TABLE 4

| Weeks | Climate (° C./% R.H.) | Packaging | Content (%) | Sum of all degradation products (%) |
|---|---|---|---|---|
| 13 | 25/60 | Glass | 101.13 | 0.43 |
| 26 | 25/60 | Glass | 101.04 | 1.29 |
| 13 | 30/60 | Glass | 100.79 | 0.97 |
| 26 | 30/60 | Glass | 99.89 | 1.93 |
| 13 | 40/75 | Glass | 96.94 | 2.37 |
| 26 | 40/75 | Glass | 98.20 | 3.60 |

COMPARATIVE EXAMPLE 2

CaHPO$_4$ Film Tablet, Batch 8782)

Film tablet comprising
1.0 mg of (R)-(−)-2-[5-(4-fluorophenyl)-3-pyridylmethylaminomethyl]chroman
100.0 mg of calcium hydrogenphosphate
10.0 mg of hydroxypropylcellulose (low degree of substitution)
6.0 mg of pre-pasted starch
1.0 mg of hydroxypropylmethylcellulose
49.75 mg of microcrystalline cellulose
1.0 mg of highly disperse silicon dioxide
3.125 mg of magnesium stearate
1.86 mg of hydroxypropylmethylcellulose
0.455 mg of Macrogol 400
1.164 mg of titanium(IV) oxide
0.233 mg of extremely finely powdered talc The film tablets are produced by granulation of the active compound with calcium hydrogenphosphate, hydroxypropylcellulose, pre-pasted starch and HPMC solution. Microcrystalline cellulose, highly disperse silicon dioxide and magnesium stearate are admixed with the granules, the resultant mixture is pressed to give tablets, coated with a suspension of titanium dioxide and talc in an HPMC/PEG solution in a drum coater and transferred into glass bottles.

After storage under defined climatic conditions for predetermined times, the film tablets are investigated with respect to active-compound content and degradation products. Storage times, climatic conditions and the amounts of active compound and degradation products measured in each case are shown in Table 5.

TABLE 5

| Weeks | Climate (° C./% R.H.) | Packaging | Content (%) | Sum of all degradation products (%) |
|---|---|---|---|---|
| 13 | 25/60 | Glass | 105.6 | 0.43 |
| 26 | 25/60 | Glass | 103.9 | 0.80 |
| 13 | 30/60 | Glass | 105.0 | 0.43 |
| 26 | 30/60 | Glass | 104.5 | 0.86 |
| 13 | 40/75 | Glass | 105.7 | 0.55 |
| 26 | 40/75 | Glass | 101.7 | 1.37 |

Investigations of the Stability of the Compositions

The stability of the compositions according to the invention is tested in durability studies. To this end, the solid compositions prepared are stored at various temperatures, removed from storage at certain times and investigated using suitable analytical methods. The climatic conditions selected are 25° C. with a relative atmospheric humidity (R.H.) of 60%, 30° C. with an R.H. of 60 or 65% and 40° C. with an R.H. of 75%. While the first-mentioned condition stands for storage at room temperature in climatic zone I and II and the second-mentioned stands for storage at room temperature in climatic zone III and IV, the last-mentioned condition is selected as stress condition in order rapidly to achieve differences with respect to stability in the various formulations. Possible instabilities are evident in (R)-(−)-2-[5-(4-fluorophenyl)-3-pyridylmethylaminomethyl]chroman principally through the formation of degradation products.

Analytical Test Methods:

Identity, purity and assay of the solid composition comprising (R)-(−)-2-[5-(4-fluorophenyl)-3-pyridylmethylaminomethyl]chroman are tested by high-performance liquid chromatography with UV detection using an RP-18 column in the high-pressure gradient system after preparation and during the stability studies. The extraction medium and mobile phase used are mixtures of acetonitrile and phosphate buffer.

The invention claimed is:

1. A solid pharmaceutical composition comprising (R)-(−)-2-[5-(4-fluorophenyl)-3-pyridylmethylaminomethyl]chroman as active compound and at least one sugar alcohol as filler.

2. A solid pharmaceutical composition according to claim 1, wherein (R)-(−)-2-[5-(4-fluorophenyl)-3-pyridylmethylaminomethyl]chroman is present as the hydrochloride salt.

3. A solid pharmaceutical composition according to claim 1, wherein the sugar alcohol present is sorbitol and/or mannitol.

4. A solid pharmaceutical composition according to claim 3, wherein the sugar alcohol mannitol is present.

5. A solid pharmaceutical composition according to claim 4, wherein mannitol is present in the form of δ-mannitol.

6. A solid pharmaceutical composition according to claim 1, wherein the sugar alcohol(s) comprises less than 0.2% by weight of reducing sugars.

7. A solid pharmaceutical composition according to claim 6, wherein the sugar alcohol(s) comprises less than 0.05% by weight of reducing sugars.

8. A solid pharmaceutical composition according to claim 1, wherein said composition is in granule, capsule or tablet form.

9. A solid pharmaceutical composition according to claim 8, wherein said composition is in the form of a tablet.

10. A solid pharmaceutical composition according to claim 9, wherein said tablet contains hydroxypropylmethylcellulose as a binder.

11. A solid pharmaceutical composition according to claim 1, wherein said composition contains 0.1 to 10% by weight of (R)-(−)-2-[5-(4-fluorophenyl)-3-pyridylmethylaminomethyl]chroman, 50 to 99.9% by weight of mannitol and 1 to 5% by weight of hydroxypropylmethylcellulose.

12. A process for the preparation of a solid pharmaceutical composition according to claim 1, comprising: subjecting a powder mixture containing (R)-(−)-2-[5-(4-fluorophenyl)-3-pyridylmethylaminomethyl]chroman and said at least one sugar alcohol to direct compression, or subjecting granules produced by means of moist or dry granulation to pressing, and subsequently optionally providing the composition with a coating.

13. A process according to claim 12, wherein the granules produced by means of moist granulation are subject to pressing.

14. A solid pharmaceutical composition according to claim 1, wherein (R)-(−)-2-[5-(4-fluorophenyl)-3-pyridylmethylaminomethyl]chroman is present as the free base or as a hydrobromide, hydrochloride, dihydrochloride, acetate, aspartate, benzoate, citrate, fumarate, glutamate, maleate, methanesulfonates, or tartrate salt.

15. A solid pharmaceutical composition according to claim 1, wherein said at least one sugar alcohol is a hexitol or pentitol.

16. A solid pharmaceutical composition according to claim 1, wherein said at least one sugar alcohol is mannitol, sorbitol, dulcitol, xylitol or ribitol.

17. A solid pharmaceutical composition according to claim 1, further comprising a binder.

18. A solid pharmaceutical composition according to claim 17, wherein said composition contains 1 to 5% by weight of said binder.

19. A solid pharmaceutical composition according to claim 1, further comprising:
   0.01 to 20% by weight of at least one disintegrant;
   0.1 to 3% by weight of at least one flow regulator; and/or
   0.1 to 5% by weight of at least lubricant.

20. A solid pharmaceutical composition according to claim 1, wherein said composition contains 0.2 to 2% by weight of (R)-(−)-2-[5-(4-fluorophenyl)-3-pyridylmethylaminomethyl]chroman, 90 to 98% by weight of mannitol, and 1.5 to 3% by weight of hydroxypropylmethylcellulose.

* * * * *